(12) United States Patent
Lee et al.

(10) Patent No.: US 9,709,540 B2
(45) Date of Patent: Jul. 18, 2017

(54) COVER DEVICE WITH ODOR DETECTOR AND ELECTRONIC DEVICE HAVING THE SAME

(71) Applicant: SAMSUNG ELECTRONICS CO., LTD., Suwon-si (KR)

(72) Inventors: Si-Hoon Lee, Yongin-si (KR); Tae-Pyeong Kim, Seongnam-si (KR); Farah Alnaimi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 77 days.

(21) Appl. No.: 14/721,390

(22) Filed: May 26, 2015

(65) Prior Publication Data

US 2015/0338385 A1    Nov. 26, 2015

(30) Foreign Application Priority Data

May 26, 2014   (KR) .................. 10-2014-0063018

(51) Int. Cl.
| | |
|---|---|
| *G01N 33/00* | (2006.01) |
| *H05K 5/03* | (2006.01) |
| *H04M 1/18* | (2006.01) |
| *H04M 1/21* | (2006.01) |
| *H04M 1/725* | (2006.01) |

(52) U.S. Cl.
CPC ..... *G01N 33/0004* (2013.01); *G01N 33/0009* (2013.01); *H04M 1/185* (2013.01); *H05K 5/03* (2013.01); *H04M 1/21* (2013.01); *H04M 1/72527* (2013.01); *Y10T 307/766* (2015.04)

(58) Field of Classification Search
CPC .... G08B 23/00; G01N 33/00; G01N 33/0004; G01N 33/0031; H04M 1/185; H05K 5/03; G06F 1/16; H04B 1/38
USPC ........................................ 73/23.34
See application file for complete search history.

(56) References Cited

U.S. PATENT DOCUMENTS

| | | | | |
|---|---|---|---|---|
| 7,160,104 B2 * | 1/2007 | Faber | ............... | F23N 5/265 |
| | | | | 431/131 |
| 8,537,020 B2 * | 9/2013 | Thorson | ............ | G01N 31/22 |
| | | | | 250/339.13 |
| 8,618,939 B2 * | 12/2013 | Nabata | ............ | A24F 47/00 |
| | | | | 340/384.3 |
| 8,784,747 B2 * | 7/2014 | Carmichael | ....... | A61L 9/04 |
| | | | | 239/34 |
| 9,438,723 B2 * | 9/2016 | Lee | ............ | H04M 1/72577 |
| 2006/0191319 A1 | 8/2006 | Kurup | | |
| 2007/0094179 A1 | 4/2007 | Ridi et al. | | |
| 2009/0293211 A1 * | 12/2009 | Spungin | ......... | A46B 15/0055 |
| | | | | 15/3 |

(Continued)

FOREIGN PATENT DOCUMENTS

KR   10-1246726 B1   3/2013

*Primary Examiner* — Lisa Caputo
*Assistant Examiner* — Octavia Hollington
(74) *Attorney, Agent, or Firm* — Sughrue Mion, PLLC

(57) ABSTRACT

A cover device including: a rear cover; a front cover rotatable with respect to the rear cover; and an odor detection module mounted to the front cover. The cover device enables miniaturization of an odor detector and ensures portability of an electronic device even through the odor detector is connected to the electronic device, and enhances the outward appearances of the electronic device, and an electronic device having the cover device.

28 Claims, 13 Drawing Sheets

(56) References Cited

U.S. PATENT DOCUMENTS

2012/0116241 A1 5/2012 Shieh et al.
2014/0134053 A1* 5/2014 Mayer ............... G01N 33/0004
 422/83

* cited by examiner

COVER DEVICE WITH ODOR DETECTOR AND ELECTRONIC DEVICE HAVING THE SAME

CROSS-REFERENCE TO RELATED APPLICATION(S)

This application claims the benefit under 35 U.S.C. §119 (a) of Korean Patent Application No. 10-2014-0063018 filed on May 26, 2014 in the Korean Intellectual Property Office, the disclosure of which is incorporated herein by reference in its entirety.

FIELD

One or more exemplary embodiments relate generally to an electronic device, and more particularly, to a cover device having an odor detector and an electronic device having the cover device.

BACKGROUND

Various electronic devices are available to users. Users access to various types of content from various types of electronic devices, such as a portable phone, an MP3 player, a Portable Multimedia Player (PMP), and an e-book reader. Diverse functions, including a camera function, a music video playback function, a multimedia playback function, and game paying function, as well as wireless transmission and reception of data, are integrated in these electronic devices. Owing to the portability, convenience, and multimedia functions of electronic devices, users may use them in diverse environment, both indoors and outdoors. As a consequence, a large number of users carry electronic devices daily.

Such an electronic device is provided with a display on its front surface to provide multi-functions. Many smartphones have a display occupying almost the entirety of its front surface, the display being responsive to a touch.

As described above, an electronic device may have various modules to allow a user to use various types of content as well as a voice call. In addition, the electronic device may have an odor detecting module, i.e., an odor detector.

Odor detectors, such as a gas/Volatile Organic Compound (VOC) sensor, may sense scent, odor, temperature, humidity, or other ambient air conditions, have been developed. An odor detector may be configured as a standalone device or in electrical or mechanical connection within an electronic device. If the odor detector is provided as a standalone device, the odor detector may sense scent, odor, temperature, humidity, or other ambient air conditions around it and may display the sensed information on a separate display window. On the other hand, if the odor detector is operated in connection to an electronic device, the odor detector may sense scent, odor, temperature, humidity, or other ambient air conditions around a user and may display the sensed information or its equivalent information on the electronic device.

In the case where the odor detector operates standalone, the odor detector should be provided with a display through which the user may view information about the ambient environment (odor, scent, temperature, humidity, or other ambient air conditions) and equipped with various parts for driving the display and displaying the sensed information on the display, such as a power supply, driver, and backlight. Due to these requirements, the size and cost of the standalone odor detector is increased.

On the other hand, in the case where the odor detector is connected to an electronic device, the odor detector may be connected to a connection port for power supply or data transmission and reception, or a connection port like an ear jack. In this case, the odor detector protrudes outward from the electronic device through the connection port, which makes the electronic device less portable and degrades an outer appearance of the electronic device. Moreover, if the electronic device connected to the odor detector is dropped or impacted, a connector of the odor detector or the connection port of the electronic device is vulnerable to damage. To use the odor detector, the odor detector must be connected to the electronic device. Frequent attachment and detachment of the odor detector to and from the electronic device increases the risk of breakage of the connector of the odor detector or the connection port of the electronic device.

If the odor detector is provided inside the electronic device, the odor detector is limited in its effectiveness in collecting ambient environment information such as odor, scent, temperature, humidity, or other ambient air conditions. As a consequence, data is difficult to detect accurately and data accuracy is decreased.

The above is presented to assist with an understanding of one or more exemplary embodiments. No determination has been made, and no assertion is made, as to whether any of the above might be applicable as prior art with regard to one or more exemplary embodiments.

SUMMARY

One or more exemplary embodiments may address the above-mentioned problems and/or disadvantages and provide the advantages described below. However, it is not necessary for an exemplary embodiment to address all of the above-mentioned problems or disadvantages, and an exemplary embodiment may not address any of the above-mentioned problems or disadvantages.

An aspect of one or more exemplary embodiments is to provide a cover device which enables miniaturization of an odor detector, ensures portability of an electronic device even though the odor detector is connected to the electronic device, and enhances the outward appearances of the electronic device, and an electronic device having the cover device.

Another aspect of one or more exemplary embodiments is to provide a cover device which is easily connected to an electronic device without adversely affecting a connection port, decreases the risk of damaging an odor detector or the electronic device when the odor detector or the electronic device is impacted, accommodates the odor detector, and ensures connection stability despite frequent attachment to or detachment from the electronic device, and an electronic device having the cover device.

Another aspect of one or more exemplary embodiments is to provide a cover device which activates an odor detector by connecting to an electronic device, has the odor detector exposed outward to enable the odor detector to easily detect accurate data of about an ambient environment (for example, odor, scent, humidity, temperature, and the like), and displays this data on the electronic device, and an electronic device having the cover device.

Another aspect of one or more exemplary embodiments is to provide a cover device with an odor detector, to which a scent cartridge is electrically connected so that the cover device may receive contents of an electronic device (for example, a rose displayed on a display of the electronic device) and provide information (for example, fragrance, odor, and the like) to a user according to the contents of the electronic device, and an electronic device having the cover device.

In accordance with an aspect of one or more exemplary embodiments, there is provided a cover device. The cover device includes: a rear cover; a front cover rotatable with respect to the rear cover; and an odor detection module mounted to the front cover.

An opening may be formed on a front surface of the front cover, and the odor detection module may be accommodated in opening.

The cover device may further include a multi-porous member disposed on a front surface of the opening configured to enable the odor detection module to detect information corresponding to an ambient environment.

The opening may include: a rear recess for detachably accommodating the odor detection module; and a front recess, having a larger area than the rear recess, for accommodating the multi-porous member.

The opening may include a plurality of porous holes.

The front cover may include: a first member having the opening; and a second member on a surface of the first member.

The odor detection module may be mounted between the first member and the second member on a rear surface of the opening.

The cover device may further include a connection module provided in the rear cover configured to connect with a connection terminal in a body of an electronic device to pair the odor detection module with the electronic device.

The connection module may include: a connection surface provided on the front cover, and configured to be electrically connected to the odor detection module when the odor detection module is mounted; a connection member provided on the rear cover and configured to be electrically connected to the odor detection module and the connection terminal of the body; and a connection line provided between the connection surface and the connection member.

The connection member may be configured to be electrically connected to at least one of a connection terminal connected at a micro Secure Digital (SD) connection port of a rear surface of the body, a connection terminal connected at a Universal Serial Bus (USB) connection port, a connection terminal connected at an ear jack connection port, and a connection terminal provided separately from connection ports on the rear surface of the body.

The connection module may be configured to wirelessly connect with the electronic device using at least one of a Near Field Communication (NFC) connection, a Bluetooth connection, and a ZigBee connection.

The cover device may further include a power supply disposed on the front cover, configured to supply power to the odor detection module.

A recess may be formed around the odor detection module inside the front cover, and the power supply may be configured to be detachably accommodated in the recess formed around the odor detection module.

The cover device may further include a scent-emitting cartridge disposed on the front cover, scent-emitting cartridge configured to emit scent.

When the rear cover is engaged with a rear surface of a body of an electronic device, the scent-emitting cartridge may be paired with the electronic device.

In accordance with another aspect of one or more exemplary embodiments, there is provided a cover device. The cover device includes: a rear cover; a front cover rotatable with respect to the rear cover and comprising an opening; an odor detection module mounted in the opening; a multi-porous member mounted in the opening and covering the odor detection module; and a connection module configured to, when the rear cover is engaged with a rear surface of a body of the electronic device, pair the odor detection module with an electronic device.

The connection module may include: a connection member disposed on the rear cover, electrically connected to the odor detection module, and configured to be electrically connected to a connection port of the body when the rear cover is engaged with the rear surface of the body of the electronic device; and a connection line provided between the connection member and the odor detection module, and configured to electrically connect the odor detection module to the connection member.

The connection module may include at least one of a Near Field Communication (NFC) chip, Bluetooth chip, and ZigBee chip.

The cover device may further include a battery on the front cover configured to supply power to the odor detection module.

In accordance with another aspect of one or more exemplary embodiments, there is provided an electronic device having a cover device including: a body; a rear cover engaged with a rear surface of the body; a front cover rotatable with respect to the rear cover and configured to cover a front surface of the body; an odor detection module mounted to the front cover; a connection module configured to pair, when the rear cover is engaged with the rear surface of the body, the odor detection module with the body; and a controller configured to control the body according to a sensed value of the odor detection module.

The body may include a rear case comprising a battery mounting space on the rear surface of the body, and the rear cover may include a cover device configured to cover the rear case.

An opening may be formed on the front cover configured to accommodate the odor detection module, and the odor detection module may be mounted in the opening.

The electronic device may further include a plurality of porous holes provided in the opening.

The electronic device may further include a multi-porous member provided in the opening, covering the odor detection module and configured to enable the odor detection module to detect information corresponding to an ambient environment.

The connection module may include: a connection member disposed on the rear cover, and configured to electrically connect to the odor detection module and a connection port of the body; and a connection line provided between the connection member and the odor detection module, and configured to electrically connect the odor detection module to the connection member.

The rear cover may be engaged with the rear surface of the body, the connection member may be electrically connected to the connection port, and the controller may be configured to receive a signal corresponding to the electrical connection between the connection member and the connection port and to control an activation of a user module corresponding to the odor detection module.

The electronic device may further include a display.

The odor detection module may be further configured to, in response to external information being supplied to the odor detection module through the opening, sense the information, and the controller may be further configured to receive a value corresponding to the sensed information and control the display to display the received value.

The connection module may be further configured to wirelessly pair the body with the odor detection module and operates using at least one of Near Field Communication (NFC), Bluetooth, and ZigBee.

The connection module may be further configured to, when the rear cover is engaged with the rear surface of the body, pair the body with the odor detection module, and the controller may be further configured to receive a pairing signal from the connection module and control an activation of a user module corresponding to the odor detection module.

The electronic device may further include a battery disposed on the front cover and configured to supply power to the odor detection module.

The electronic device may further include: a display; and a scent-emitting cartridge provided in on the front cover, and configured to emit scents.

When the rear cover is engaged with the rear surface of the body, the scent-emitting cartridge may be connected to the body, and the controller may be further configured to control the scent-emitting cartridge according to information displayed on the display.

In accordance with an aspect of one or more exemplary embodiments, there is provided a cover device. The cover device includes: a rear cover configured to engage with a back surface of an electronic device; a front cover rotatably connected to the rear cover; and an odor detector mounted on the front cover, the odor detector being configured to sense information about an ambient environment, and to operate, when the rear cover is engaged with the back surface of the electronic device, under a control of the electronic device.

The cover device may further include a scent-emitting cartridge configured to emit scents, and to operate, when the rear cover is engaged with the back surface of the electronic device, under a control of the electronic device.

The cover device may further include a connector configured to, in response to the rear cover being engaged with the back surface of the electronic device, pair the odor detector with the electronic device.

The connector may be further configured to, in response to pairing the odor detector with the electronic device, transmit a notification to the electronic device.

The electronic device may be configured to, in response to receiving the notification, execute a user module and control the odor detector based on the user module.

The cover device may further include a connector configured to, in response to the rear cover being engaged with the back surface of the electronic device, pair the odor detector and the scent-emitting cartridge with the electronic device.

The connector may be further configured to, in response to pairing the odor detector and the scent-emitting cartridge with the electronic device, transmit a notification to the electronic device.

The electronic device may be configured to, in response to receiving the notification, execute a user module and control the odor detector and the scent-emitting cartridge based on the user module.

Other aspects, advantages, and salient features of one or more exemplary embodiments will become apparent to those skilled in the art from the following detailed description, which, taken in conjunction with the accompanying drawings, discloses certain exemplary embodiments.

BRIEF DESCRIPTION OF THE DRAWINGS

The above and other aspects, features and advantages of certain exemplary embodiments will be more apparent from the following description taken in conjunction with the accompanying drawings, in which.

DETAILED DESCRIPTION

Figures 1A, 1B:
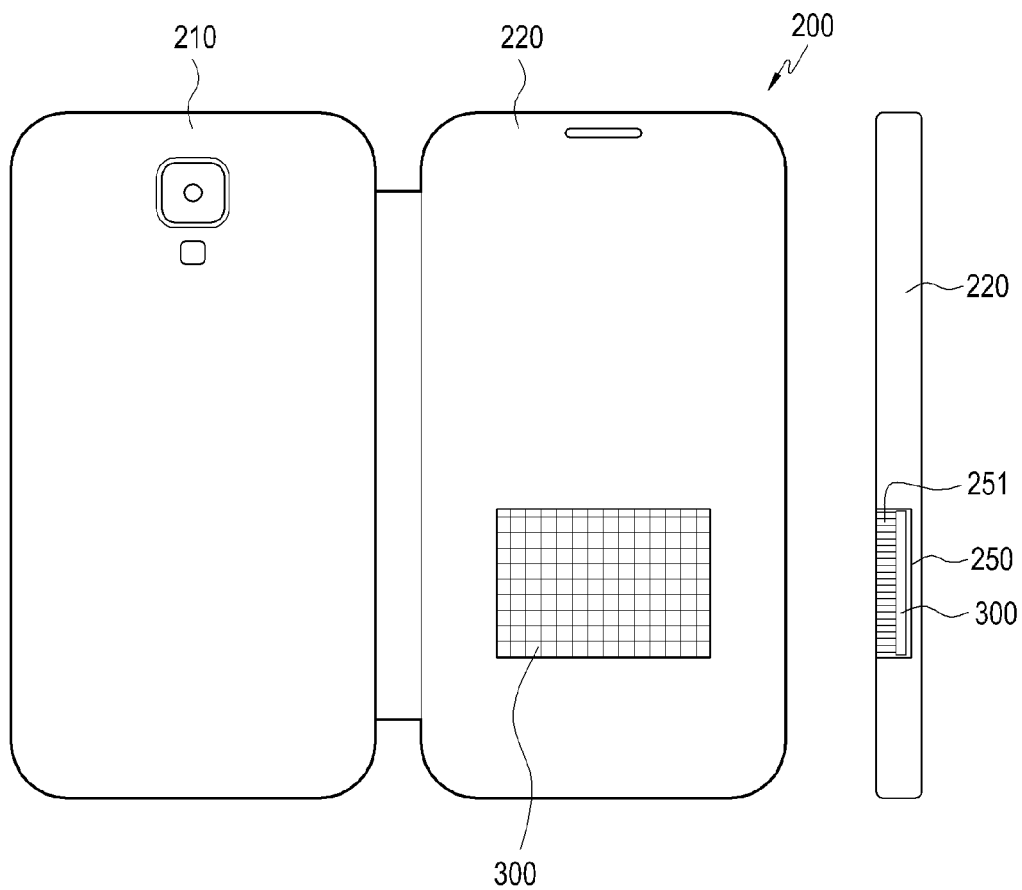
FIGS. 1A and 1B illustrate a cover device according to an exemplary embodiment.

The following description with reference to the accompanying drawings is provided to assist in an understanding of various exemplary embodiments as defined by the claims and their equivalents. It includes various specific details to assist in that understanding but these are to be regarded as merely exemplary. Accordingly, those of ordinary skilled in the art will recognize that various changes and modifications to the corresponding embodiments In addition, descriptions of well-known functions and constructions may be omitted for clarity and conciseness.

The terms and words used in the following description and claims are merely used to enable a clear and consistent understanding of embodiments and should not be considered limiting. It should be apparent to those skilled in the art that the following description of exemplary embodiments is provided for illustrative purposes only, and should not be construed as limiting the claims and their equivalents.

It is to be understood that the singular forms "a," "an," and "the" include plural referents unless the context clearly dictates otherwise. Thus, for example, reference to "a component surface" includes reference to one or more of such surfaces.

Further, throughout the drawings, like reference numerals will be understood to refer to like parts, components, and structures.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

An electronic device according to one or more exemplary embodiments may be any of a terminal, a portable terminal, a mobile terminal, a communication terminal, a portable communication terminal, a portable mobile terminal, and a display device.

For example, the electronic device may be at least one of a smart phone, a portable phone, a navigation device, a game console, a Television (TV), an in-vehicle head unit, a laptop computer, a tablet computer, a Portable Multimedia Player (PMP), and a Personal Digital Assistant (PDA). The electronic device may be a pocket-size portable communication terminal having wireless communication functionality.

The electronic device may be a flexible device or a flexible display device.

Now, a description will be given of a cover device and an electronic device having the cover device according to various exemplary embodiments.

FIGS. 1A and 1B illustrate a cover device according to an exemplary embodiment.

Referring to FIG. 1A, a cover device 200 may include a rear cover 210 and a front cover 220 having an odor detection module 300, i.e., an odor detection device, an odor detector, an odor detecting module, or an odor detecting device, mounted on it. The cover device 200 may further include a connection module, i.e., a connector, for electrically connecting the odor detection module 300 to a body 100 of an electronic device by pairing, when the cover device 200 is engaged with the electronic device. The cover device 200 may be a flip cover.

The front cover 220 may be rotatably connected to the rear cover 210 and may cover a front surface of the body 100. The odor detection module 300 is mounted on an outer surface of the front cover 220, exposed outward. The front cover 220 is provided with an opening 250 in which the odor detection module 300 is mounted and which is opened so that information about an ambient environment may be detected by the odor detection module 300.

As illustrated in FIG. 1B, the opening 250 may include a plurality of porous holes 251 through which information about an ambient environment may be introduced to the odor detection module 300 mounted in the opening 250. For example, ambient air may be able to interact with the odor detection module 300 through the porous holes 251. However, this is merely an example.

Figures 2A, 2B:
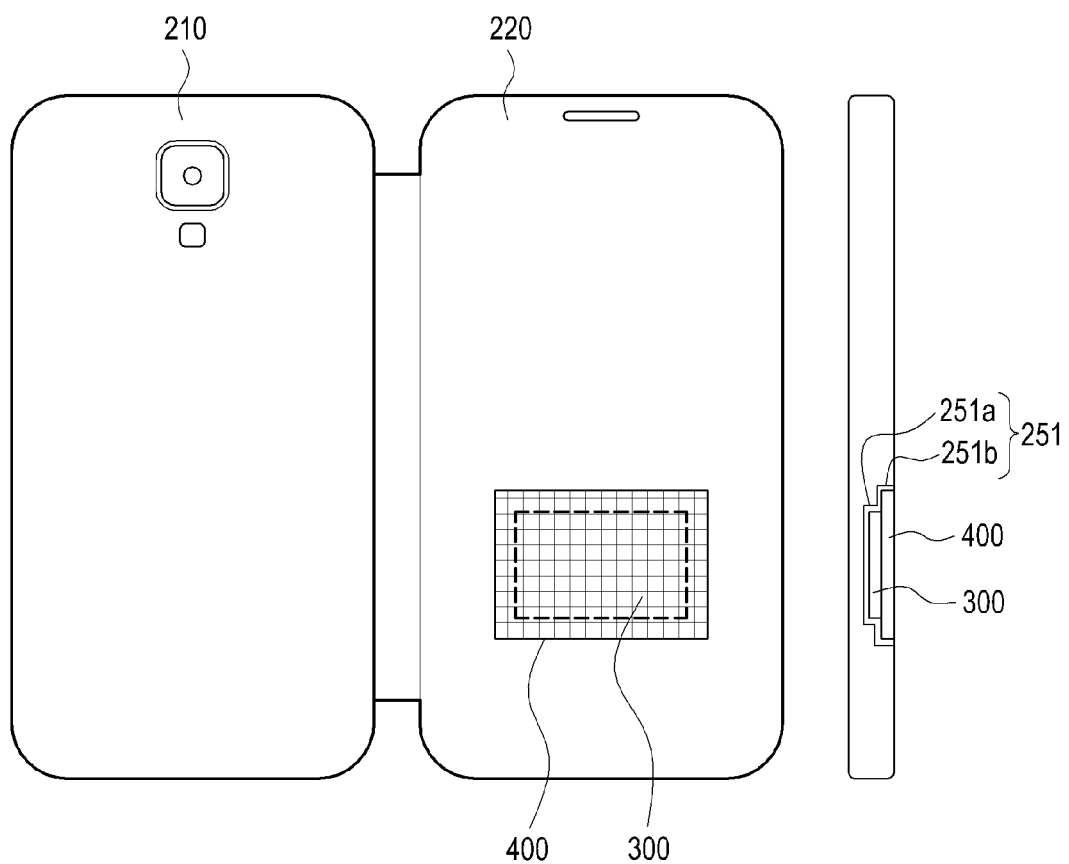
FIGS. 2A and 2B illustrate a cover device with a multi-porous member in an opening according to an exemplary embodiment.

FIGS. 2A and 2B illustrate a cover device with a multi-porous member in an opening an according to an exemplary embodiment.

The cover device 200 illustrated in FIGS. 2A and 2B may be similar to the cover device 200 illustrated in FIGS. 1A and 1B. The opening 250 may be shaped into a recess opened from the front surface of the front cover 220 and a multi-porous member 400 may be mounted in the opening 250.

Referring to FIG. 2B, the opening 250 may be provided on the front surface of the front cover 220, and the odor detection module 300 and the multi-porous member 400 may be sequentially stacked in the opening 250.

The opening 250 may include a rear recess 251a and a front recess 251b and may be opened from the front surface of the front cover 220. The rear recess 251a may be formed in a size and shape corresponding to a size and shape of the odor detection module 300, so that the odor detection module 300 may be detachably mounted in the rear recess 251a. The front recess 251b may be formed in a larger size than the rear recess 251a and thus stepped up to the rear recess 251a. The multi-porous member 400 may be mounted in the rear recess 251a to allow the collection of ambient environment information by the odor detection module 300. While the rear recess 251a and the front recess 251b are described as stepped, the opening 250 is not limited to specific shapes and sizes. For example, if the odor detection module 300 is formed in a smaller size than the multi-porous member 400, the rear recess 251a may be formed in a smaller size than the front recess 251b. However, if the odor detection module 300 and the multi-porous member 400 are of the same size, the rear recess 251a and the front recess 251b may be formed in the same size.

Figure 10:
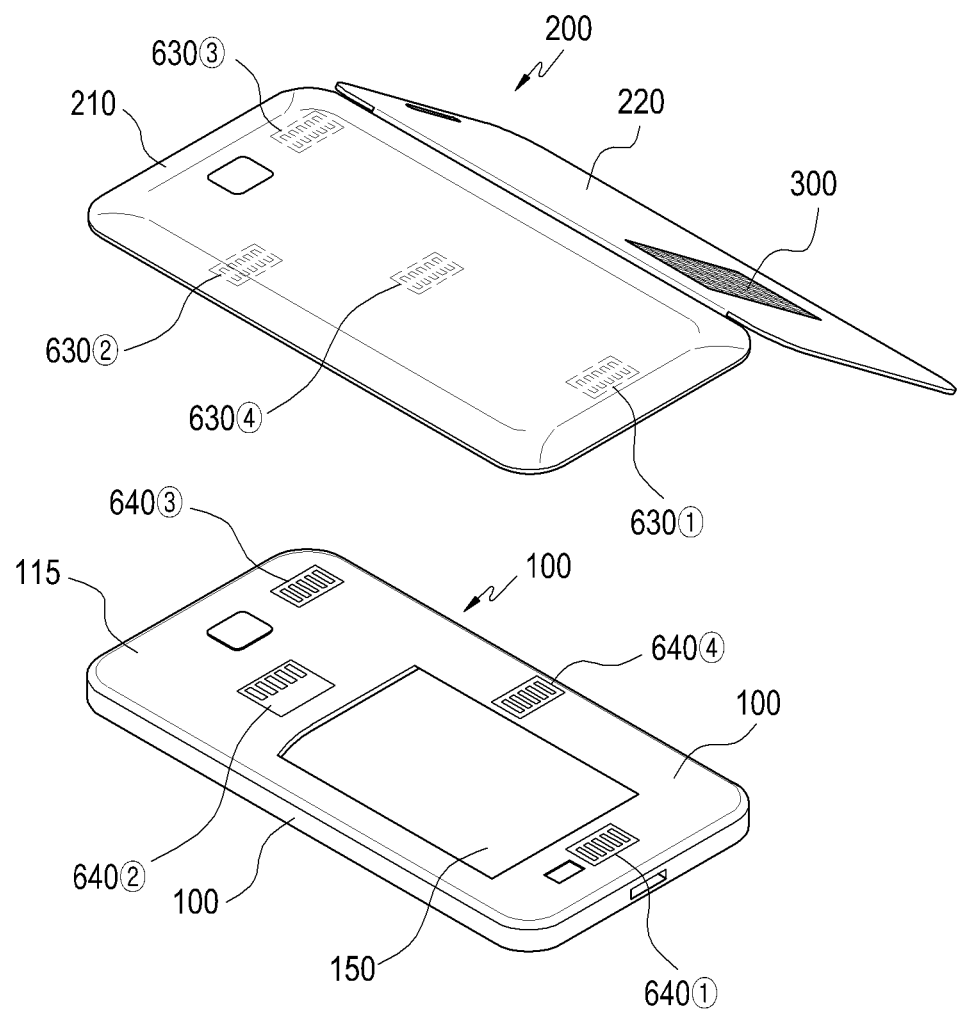
FIG. 10 illustrates various structures for wired connections of an electronic device to a cover device according to various exemplary embodiments.
Figure 11:
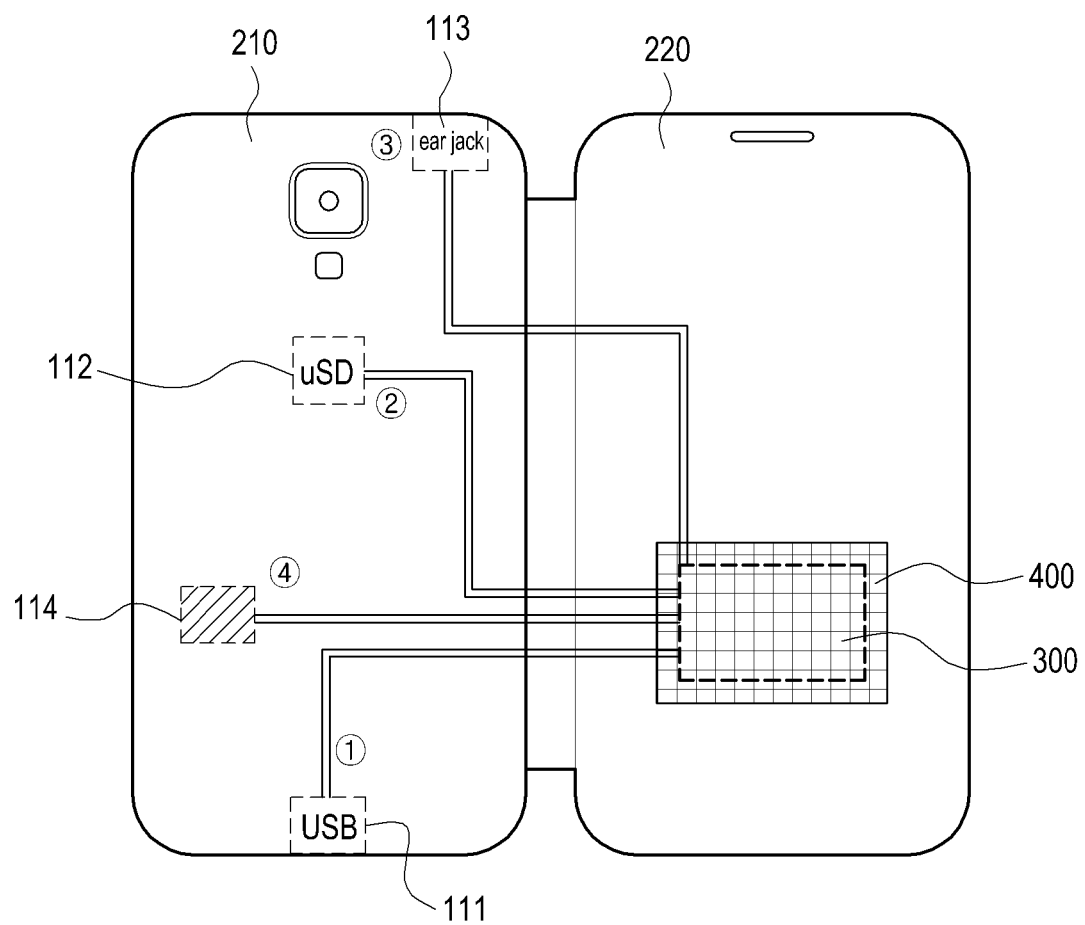
FIG. 11 illustrates a state of wired connection between a body and an odor detection module in an electronic device according to an exemplary embodiment.
Figure 12:
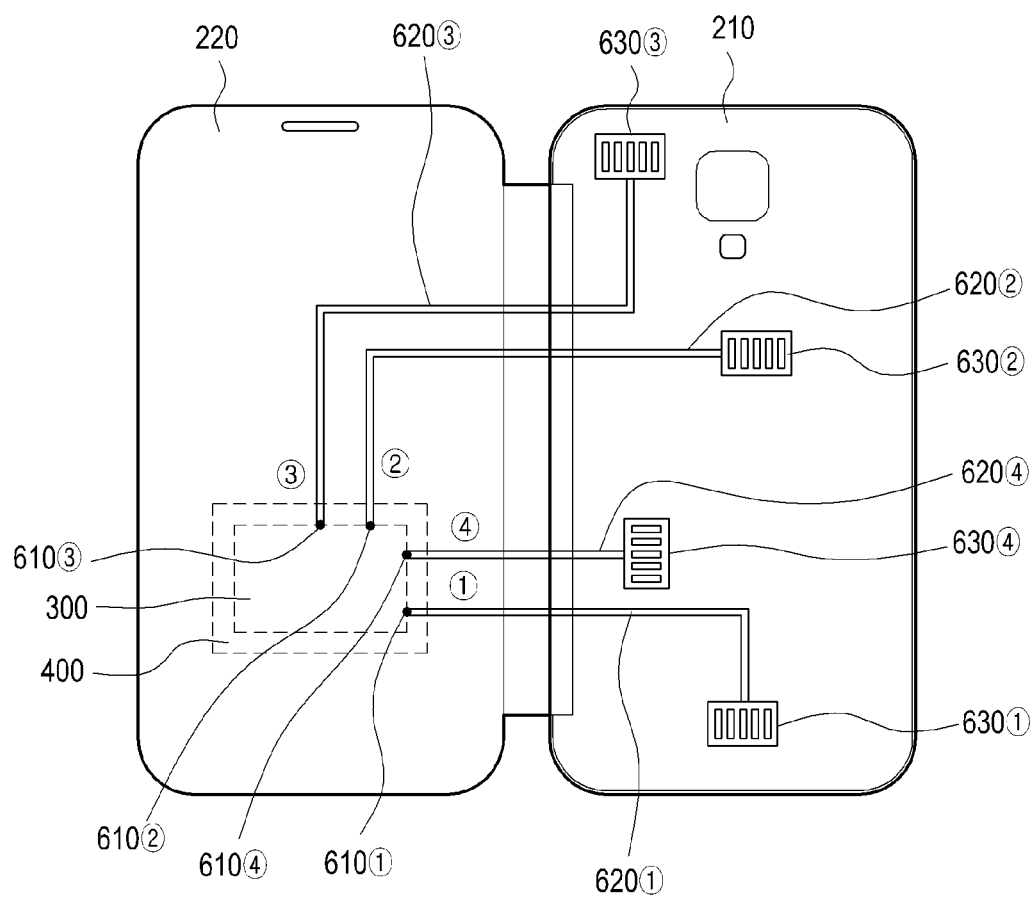
FIG. 12 illustrates an inner surface of a cover device according to an exemplary embodiment.

Further, when the cover device 200 is engaged with the body 100, the odor detection module 300 may be electrically connected to the body 100 through a wired structure through a connection surface 610 formed in the rear recess 251a (FIGS. 10-12). The connection surface 610 may be connected to connection members 630①, 630②, 630③, and 630④ via connection lines 620①, 620②, 620③, and 620④. The connection members 630①, 630②, 630③, and 630④ may be electrically engaged with connection terminals 640①, 640②, 640③, and 640④ of the body 100 so that a signal value detected by the odor detection module 300 may be applied to the body 100.

Figures 3A, 3B, 3C:
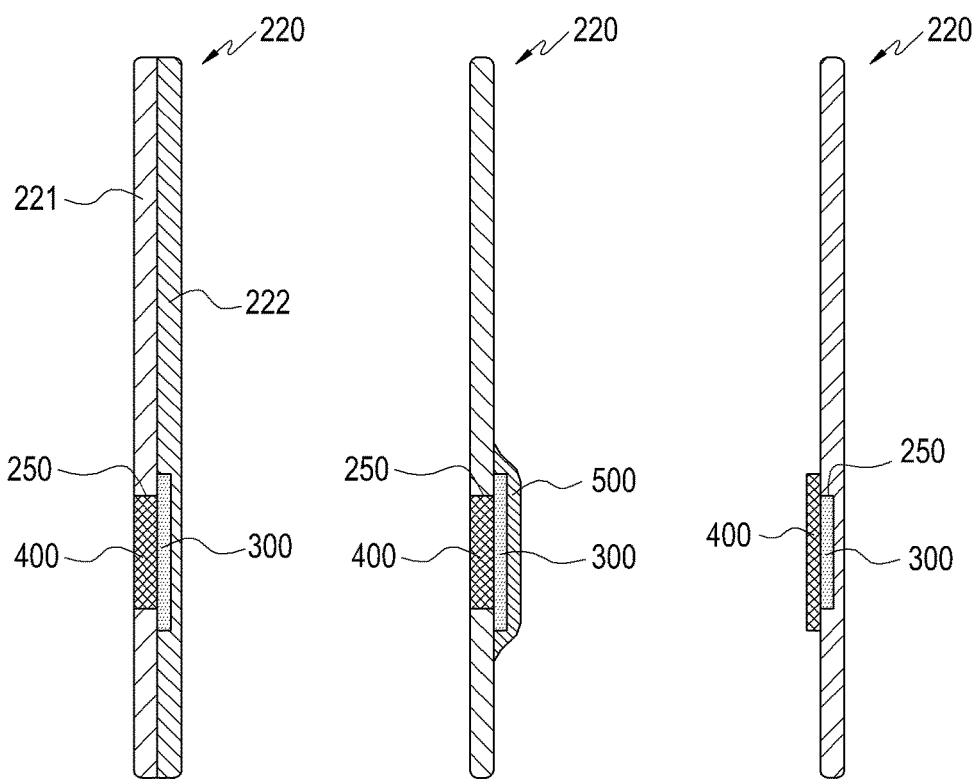
FIGS. 3A, 3B, and 3C illustrate an odor detection module that may be mounted on a front cover of a cover device according to various exemplary embodiments.
Figure 4:
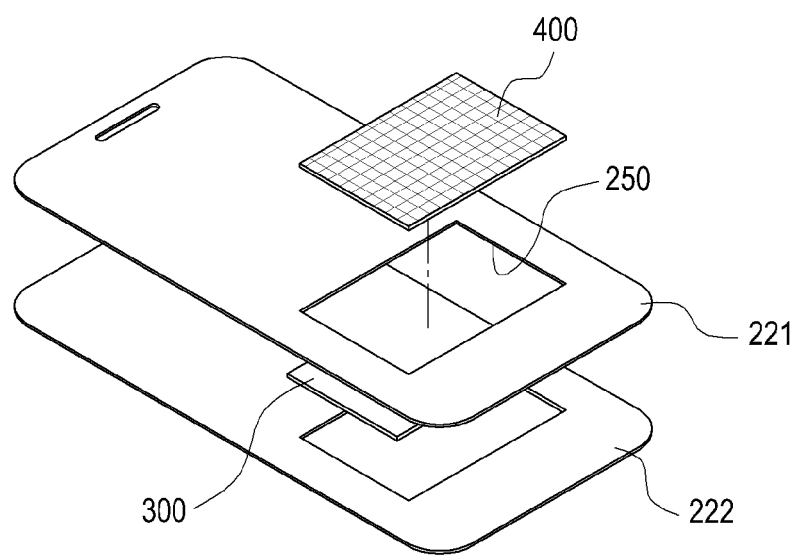
FIG. 4 is an exploded perspective view of the front cover according to the exemplary embodiment illustrated in FIG. 3A.

FIGS. 3A, 3B, and 3C illustrate an odor detection module that may be mounted on a front cover of a cover device according to various exemplary embodiments, and FIG. 4 is an exploded perspective view of the front cover according to the exemplary embodiment illustrated in FIG. 3A.

According to embodiments, various shapes are available for the front cover 220 for accommodating the odor detection module 300.

Referring to FIGS. 3A and 4, the front cover 220 may include a first member 221 and a second member 222. The odor detection module 300 may be mounted between the first member 221 and the second member 222. The first member 221 serves as the front surface of the front cover 220. The opening 250 having the porous holes 251 or the multi-porous member 400 may be formed in the first member 221. According to an exemplary embodiment, the opening 250 is a penetrating hole and the multi-porous member 400 is fit into the opening 250.

The second member 222 is provided on one surface of the first member 221, to serve as an inner surface of the front cover 220, facing a display 120 formed on the front surface of the body 100.

The odor detection module 300 may be mounted between the first member 221 and the second member 222 on the rear surface of the opening 250 of the first member 221.

Referring to FIG. 3B, the opening 250 may penetrate through the inner and outer surfaces of the front cover 220, and an engagement member 500 may be provided on the rear surface of the opening 250 to ensure engagement of the odor detection module 300 and prevent interference between the odor detection module 300 and the display 120 of the body 100. The porous holes 251 or the multi-porous member 400 may be provided in the opening 250. According to an exemplary embodiment, the opening 250 is a penetrating hole and the multi-porous member 400 is fit in the opening 250. The odor detection module 300 may be mounted on the rear surface 250 of the opening 250, that is, on the inner surface of the front cover 220. The engagement member 500 is provided to stably engage the odor detection module 300 with the inner surface of the front cover 220 and prevent interference between the odor detection module 300 protruding from the inner surface of the front cover 220 and the display 120 formed on the front surface of the body 100.

Referring to FIG. 3C, the opening 250 may be a recess opened from the front surface of the front cover 220. The odor detection module 300 may be mounted in the opening 250. The opening 250 may have a size and shape that enables a mounting of the odor detection module 300. The multi-porous member 400 may be engaged with the front surface of the front cover 220 along the periphery of the opening 250, to cover the opening 250.

As illustrated with reference to FIGS. 3A to 4, many modifications or variations may be made to the shape, structure, or configuration of the front cover 220 for mounting the odor detection module 300, taking into account the design of the front cover 220 and easy mounting and assembly of the odor detection module 300.

As the odor detection module 300 is exposed to the outside through the opening 250, the odor detection module 300 may sense information about an ambient environment. The odor detection module 300 may include a Gas/Volatile Organic Compound (VOC) sensor. Since the odor detection module 300 is provided on the front cover 220, there is no need for separately carrying an odor detection module 300. When the cover device 200 is engaged with the electronic device, the odor detection module 300 may be paired with the electronic device through wires and/or wirelessly, to thereby sense scent, odor, temperature, humidity, or other ambient air conditions in an ambient environment.

Figure 15:
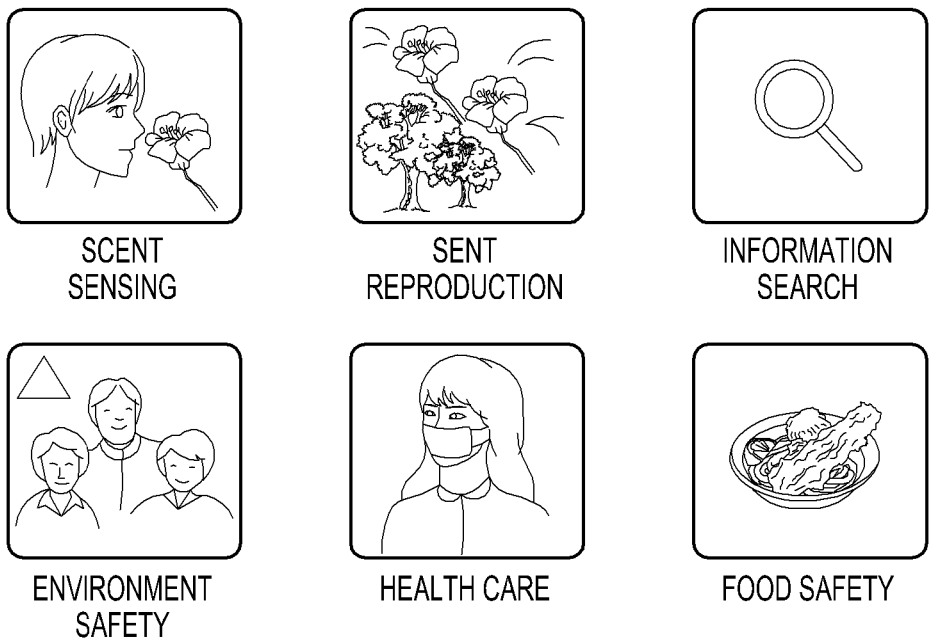
FIG. 15 illustrates use states of an odor detection module in a cover device according to an exemplary embodiment.

As illustrated in FIG. 15, the odor detection module 300 may sense information about the ambient environment, sense or reproduce scent based on the sensed information, search for information, provide information such as environment safety information, verify food safety, and provide health care information according to the ambient environment information.

Figure 5:
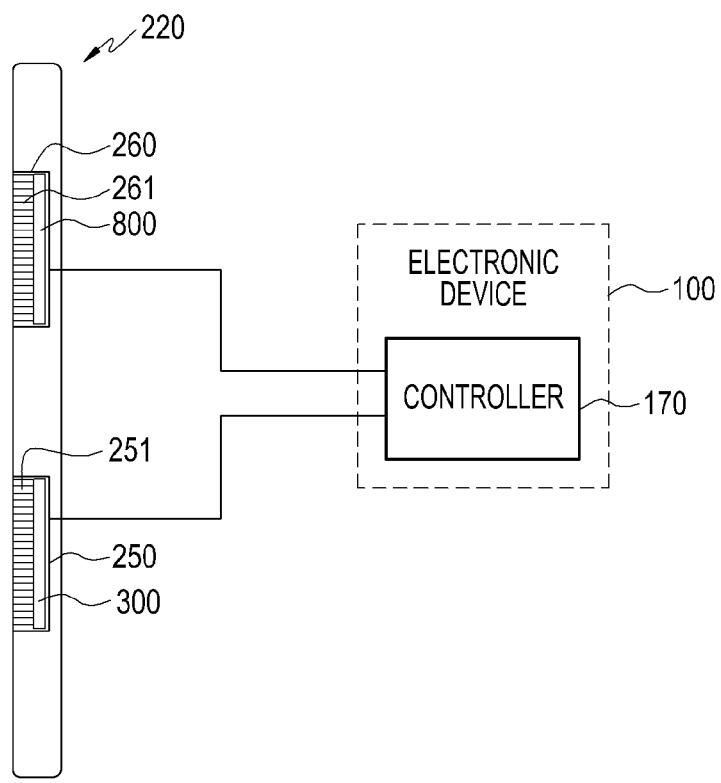
FIG. 5 illustrates a cover device having a cartridge mounted on a front cover according to an exemplary embodiment.

FIG. 5 illustrates a cover device having a cartridge mounted on a front cover according to an exemplary embodiment.

Referring to FIG. 5, a cartridge 800 may be provided in the vicinity of the odor detection module 300 behind the front cover 220 in order to emit scent. An additional opening 260 (hereinafter, referred to as a second opening 260) may be formed in the front cover 220, for detachably accommodating the cartridge 800.

A plurality of porous holes 261 may be formed into the front surface of the front cover 220 in the second opening 260 and a mounting space of the cartridge 800 may be formed in the porous holes 261. When the rear cover 210 is engaged with the rear surface of the body 100 of the electronic device, the cartridge 800 may be paired with the body 100 and may be electrically connected to the odor detection module 300. The cartridge 800 may include one or more of a scent ample, a scent sponge, and a scent capsule. When the cover device 200 is engaged with the electronic device, the cartridge 800 may be set to an active state so that it may operate. Accordingly, the controller 170 may provide information related to scent corresponding to information displayed on the display 120 and control the cartridge 800 according to the displayed information.

Figure 6A:
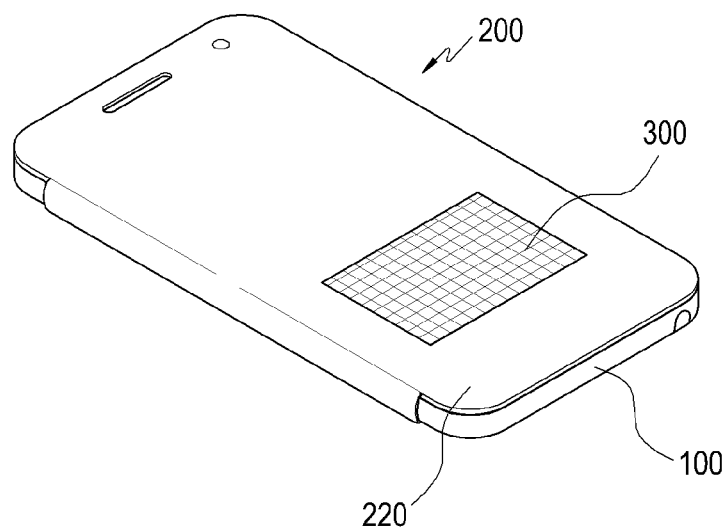
FIGS. 6A and 6B illustrate an electronic device having a cover device according to an exemplary embodiment.
Figure 6B:
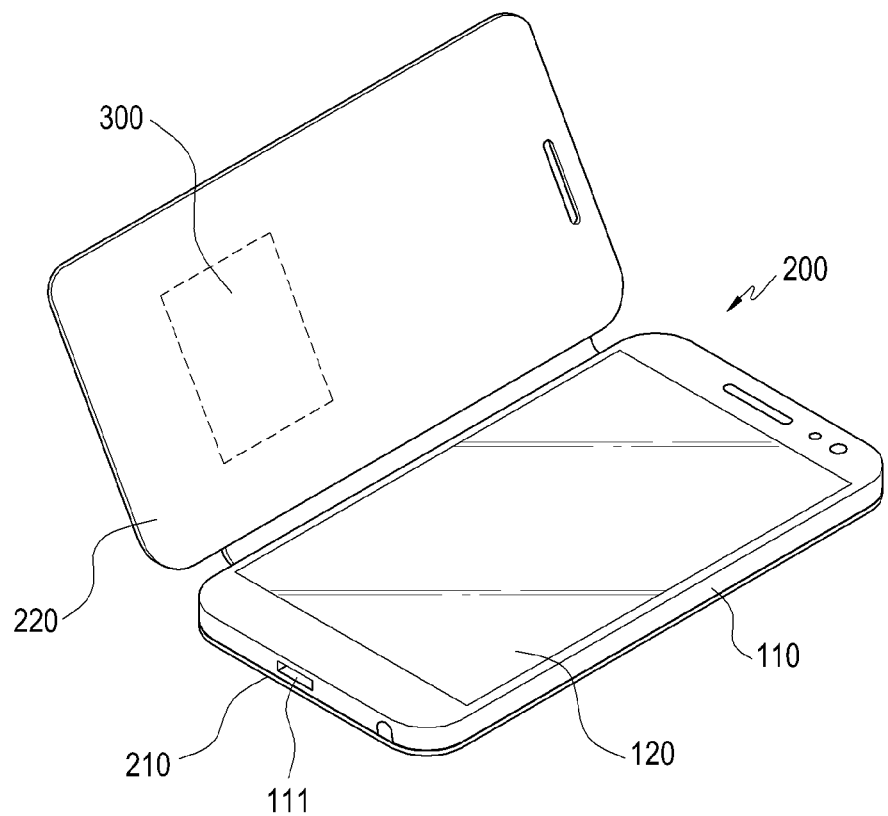
Figure 7A:
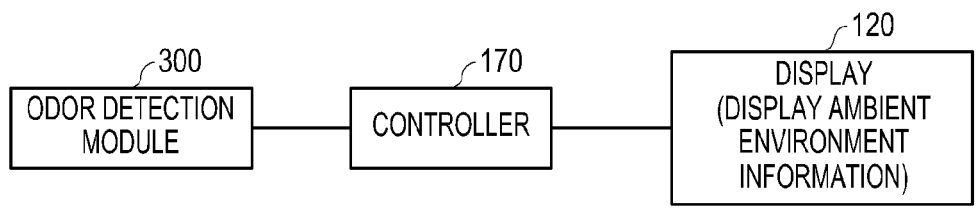
FIGS. 7A and 7B are block diagrams of an electronic device having a cover device according to various exemplary embodiments.
Figure 7B:
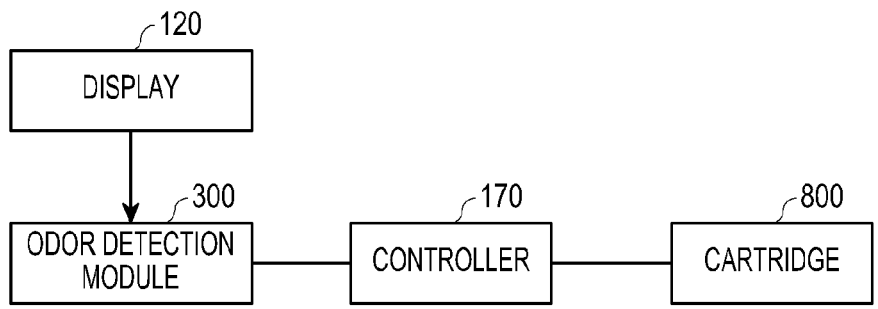

FIGS. 6A and 6B illustrate an electronic device having a cover device according to one an exemplary embodiment, and FIGS. 7A and 7B are block diagrams of an electronic device having a cover device according to various exemplary embodiments.

Referring to FIGS. 6A, 6B, and 7A, an electronic device having the cover device 200 according to an exemplary embodiment may include the body 100 and the cover device 200 that covers the front and rear surfaces of the body 100 and has the odor detection module 300 mounted in it. Various parts for executing multi-functions of the electronic device, such as a circuit board for driving the various parts, a battery 150 for supplying power (FIG. 10), and the controller 170 for controlling the electronic device, may be included in the body 100.

The body 100 may be a structure such as a smartphone, a portable phone, a navigation device, a game console, a TV, a vehicle-mounted head unit, a laptop computer, a tablet computer, a PMP, or a PDA.

The body 100 may have a rectangular shape, but this is merely an example. The display 120 may be provided on a front surface of the body 100, so that a user may view a screen and enter an input. A rear case 115 having a mounting space for the battery 150 may be engaged with the rear surface of the body 100.

When the cover device 200 is engaged with the body 100, the controller 170 may recognize the engagement and control an activation of a user module corresponding to the odor detection module 300 along with the engagement of the odor detection module 300 so that the user module may be operated. The controller 170 may control the display 120 to display information corresponding to a signal value sensed by the odor detection module 300.

Referring to FIG. 7B, if the cartridge 800 is provided on the front cover 220 along with the odor detection module 300, the controller 170 may control the cartridge 800 based on scent-related information included in information displayed on the display 120. For example, the controller 170 may control the cartridge to emit a scent corresponding to scent-related information displayed on the display 120, or in accordance with a user command.

Connection modules, i.e., connectors, may be provided in the body 100 of the electronic device and the cover device 200. The odor detection module 300 may be electrically connected to the body 100 (refer to FIGS. 8A to 12). The connection modules may be provided so that when the rear cover 210 is engaged with the rear surface of the body 100 of the electronic device, the odor detection module 300 may be paired with the body 100 through the connection modules.

The connection modules will be described below in greater detail with reference to FIGS. 8A to 12.

Figure 8A:
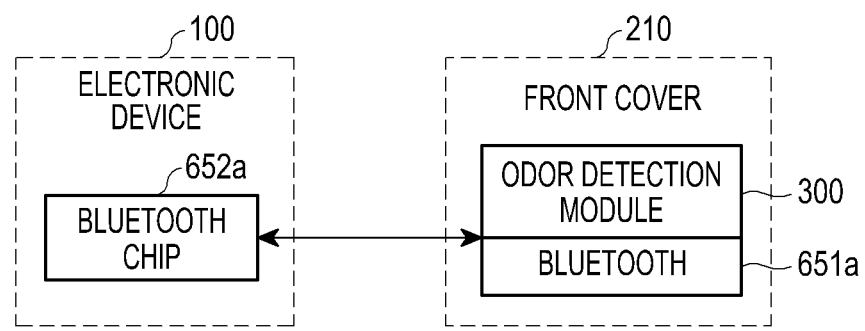
FIGS. 8A and 8B are block diagrams of an electronic device connected to a cover device according to various exemplary embodiments.
Figure 8B:
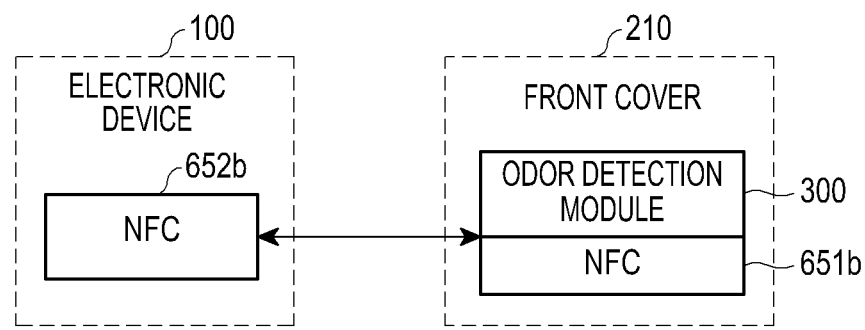
Figure 9:
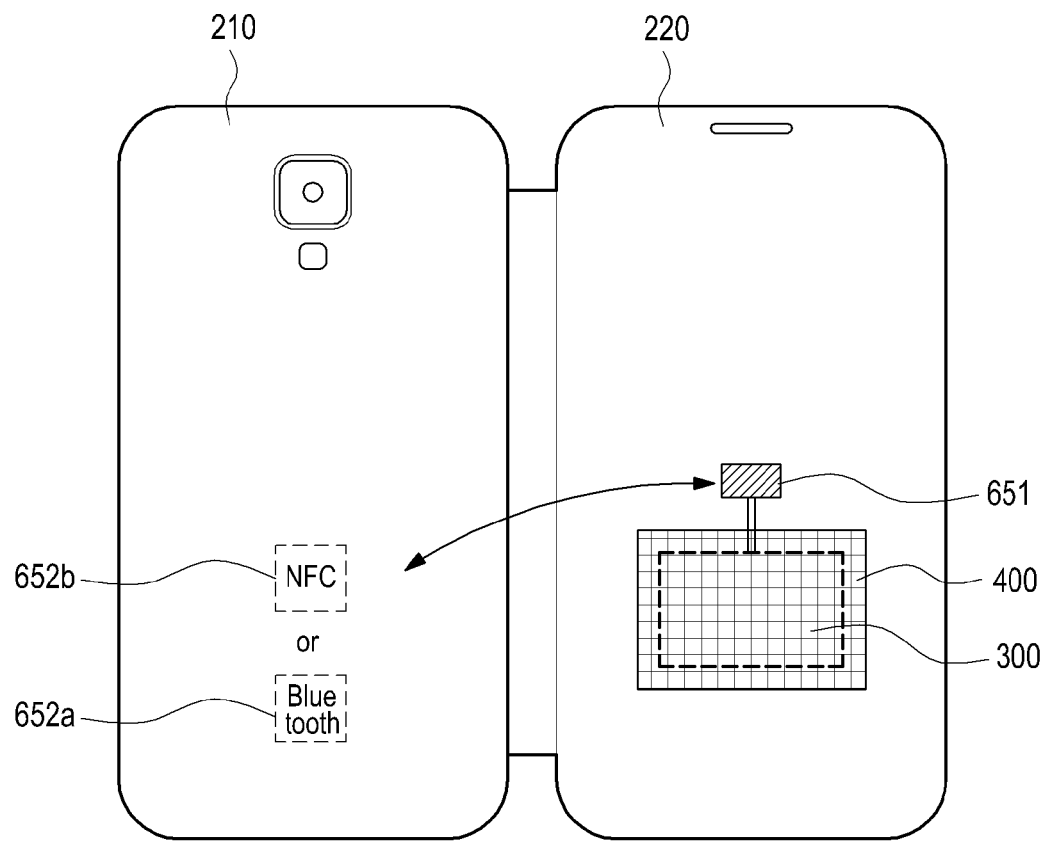
FIG. 9 illustrates connecting an electronic device to a cover device according to an exemplary embodiment.

FIGS. 8A and 8B are block diagrams of an electronic device connected to a cover device according to various exemplary embodiments, and FIG. 9 illustrates connecting an electronic device to a cover device according to an exemplary embodiment.

Referring to FIGS. 8A, 8B, and 9, the body 100 may include a Bluetooth module 652a, a Near Field Communication (NFC) module 652b, or a wireless communication module, such as a Zigbee module to enable wireless transmission and reception between the electronic device and an external device (the cover device 200 having the odor detection module 300 in an embodiment). The Bluetooth module 652a, Near Field Communication (NFC) module 652b, and wireless communication module may include a Bluetooth chip, a NFC chip, or a wireless communication chip, respectively. The cover device 200 may be provided with a Bluetooth module 651a, an NFC module 651b, or a wireless communication module near the odor detection module 300 on the front cover 220. The Bluetooth module 652a, the NFC module 652b, and the wireless communication module may pair with the Bluetooth module 652a, Near Field Communication (NFC) module 652b, or wireless communication module of the body 200, respectively. If the above wireless communication modules are activated, a detection value from the odor detection module 300 may be supplied to the controller 170 by wireless pairing between the wireless communication modules.

FIG. 10 various structures for wired connections of an electronic device to a cover device according to various exemplary embodiments, FIG. 11 illustrates a state of wired connection between a body and an odor detection module in an electronic device according to an exemplary embodiment, and FIG. 12 illustrates an inner surface of a cover device according to an exemplary embodiment.

Referring to FIGS. 10, 11, and 12, various structures for electrically connecting the cover device to the body of the electronic device in a wired manner are described.

Four connection terminals 640①, 640②, 640③, and 640④ may be provided on a rear surface of the body of the electronic device. For example, the connection terminal 640① is connected near a Universal Serial Bus (USB) connection port 111 of the body 100, the connection terminal 640② is connected near a micro Secure Digital (SD) connection port 112 on the rear surface of the body 100, the connection port 640③ is connected near an ear-jack connection port 113, and the connection terminal 640④ is provided separately from connection terminals on the rear surface of the body 100. While four connection modules labeled by ① to ④ are shown as provided on the rear surface of the cover device 200 and the body 100, this is merely an example, and one or more connection modules may be provided in the body.

The connection terminal 640① (hereinafter, referred to as the first terminal 640①) may extend from the USB connection port 111 at a predetermined position of the body 100, which will be connected to an external power source or a data cable, exposed on a surface of the rear case 115. The connection member 630① may be provided in correspondence with the position of the first terminal 640① on the inner surface of the rear cover 210. The connection line 620① may be provided to connect the odor detection module 300 provided on the front cover 220 to the first terminal 640① provided on the rear cover 210 through the connection member 630①. When the rear cover 210 is engaged with the rear surface of the body 100, covering the rear case 115 of the body 100, the connection member 630① of the rear cover 210 contacts the first terminal 640① exposed on the surface of the rear case 115. Accordingly, the odor detection module 300 may be driven in electrical connection with the body 100.

When the connection member 630① is electrically connected to the first terminal 640①, a signal generated upon the engagement between the connection member 630① and the first terminal 640① may be supplied to the controller 170. The controller 170 may control an activation of the odor detection module 300 in response to receiving the connection signal. The controller 170 may control an operation of the odor detection module 300 based on a user module corresponding to the odor detection module 300.

The connection terminal 640② (hereinafter, referred to as the second terminal 640②) may extend from the micro SD connection port 112 at one portion of the rear case 115, exposed on the surface of the rear case 115. The connection member 630② may be provided in correspondence with the position of the second terminal 640② on the inner surface of the rear cover 210. When the rear cover 210 is engaged with the rear surface of the body 100, covering the rear case 115 of the body 100, the connection member 630② of the rear cover 210 contacts the second terminal 640② exposed on the surface of the rear case 115. Accordingly, the odor detection module 300 may be driven in electrical connection with the body 100.

When the connection member 630② is electrically connected to the second terminal 640②, a signal generated upon the engagement between the connection member 630② and the second terminal 640② may be supplied to the controller 170. The controller 170 may control an activation and operation of the odor detection module 300.

The connection terminal 640③ (hereinafter, referred to as the third terminal 640③) may extend from the connection port 113 of an external device, such as an ear jack, provided at one portion of the body 100, exposed on the surface of the rear case 115. The connection member 630③ may be provided in correspondence with the position of the third terminal 640③ on the inner surface of the rear cover 210. The connection line 620③ may be provided to connect the odor detection module 300 provided on the front cover 220 to the third terminal 640③ provided on the rear cover 210. When the rear cover 210 is engaged with the rear surface of the body 100, covering the rear case 115 of the body 100, the connection member 630③ of the rear cover 210 contacts the third terminal 640③ exposed a the surface of the rear case 115. Accordingly, the odor detection module 300 may be driven in electrical connection with the body 100.

When the connection member 630③ is electrically connected to the third terminal 640③, a signal generated upon the engagement between the connection member 630③ and the third terminal 640③ may be supplied to the controller 170, and the controller 170 may control an activation of the odor detection module 300.

The connection terminal 640④ (hereinafter, referred to as the fourth terminal 640④) may be provided separately from the USB connection port 111, the USD connection port 112, or the ear jack connection port 113. The connection member 630④ may be provided in correspondence with the position of the fourth terminal 640④ on the inner surface of the rear cover 210. The connection line 620④ may be provided to electrically connect the odor detection module 300 provided on the front cover 220 to the fourth terminal 640④ provided on the rear cover 210. When the rear cover 210 is engaged with the rear surface of the body 100, covering the rear case 115 of the body 100, the connection member 630④ of the rear cover 210 contacts the fourth terminal 640④ exposed on the surface of the rear case 115. Accordingly, the odor detection module 300 may be driven in electrical connection with the body 100.

When the connection member 630④ is electrically engaged with the fourth terminal 640④, a signal generated upon the engagement between the connection member 630④ and the fourth terminal 640④ may be supplied to the controller 170, and the controller 170 may control an activation and operation of the odor detection module 300.

The electronic device having the cover device 200 according to various exemplary embodiments is configured so that when the cover device 200 is engaged with the electronic device, the odor detection module 300 is connected to the body 100 either through wires or wirelessly and driven by power from the electronic device. However, power supply to the odor detection module is not limited to power from the electronic device.

Figure 13A:
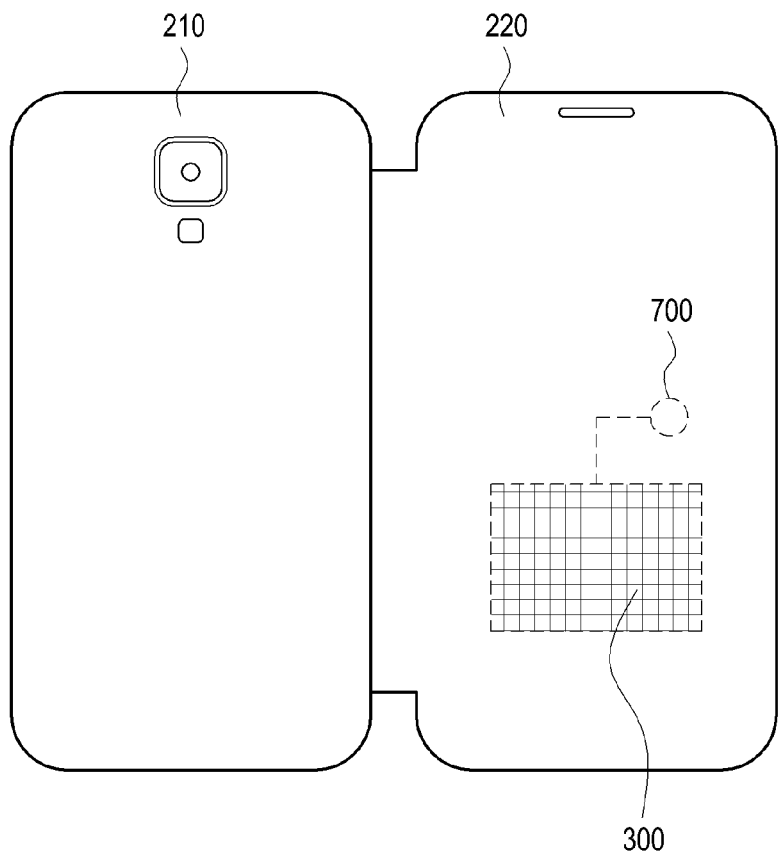
FIGS. 13A and 13B illustrate a cover device in which a power supply is separately provided to an odor detection module according to an exemplary embodiment.
Figure 13B:
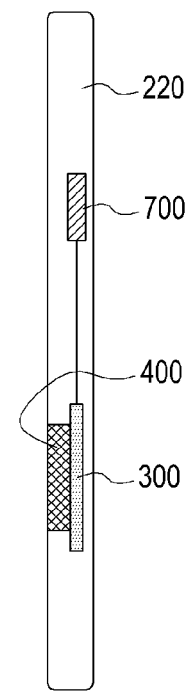

FIGS. 13A and 13B illustrate a cover device in which a power supply is separately provided to an odor detection module according to an exemplary embodiment.

Referring to FIGS. 13A and 13B, the front cover 220 may include a power supply 700 for separately supplying power to the odor detection module 300. That is, the power supply 700 is electrically connected to the odor detection module 300 and supplies operational power to the odor detection module 300. In the foregoing exemplary embodiments, the odor detection module 300 uses power from the electronic device. The use of the odor detection module 300 may lead to fast depletion of the battery 150 of the electronic device, especially in comparison with operating without the odor detection module 300. However, the power consumption of the battery 150 of the electronic device may be minimized by separately providing a power supply 700 for operating the odor detection module 300.

Figure 14:
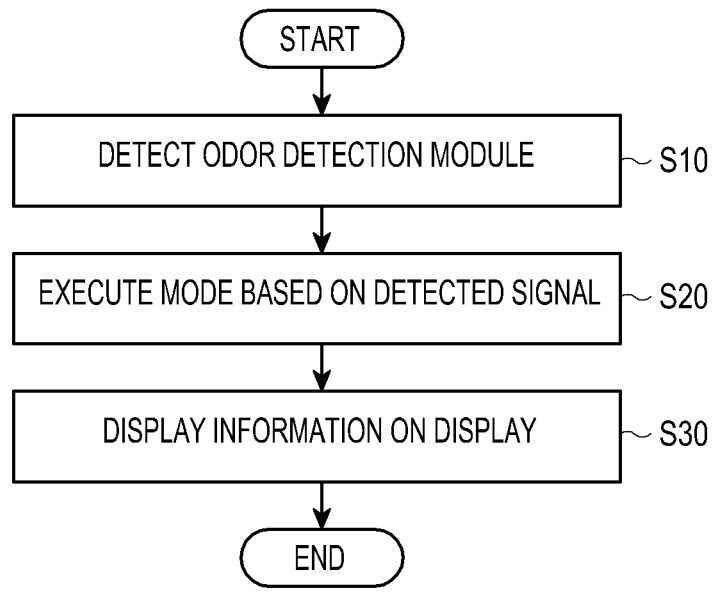
FIG. 14 is a flowchart of an operation for driving an electronic device having a cover device according to an exemplary embodiment.

FIG. 14 is a flowchart of an operation for driving an electronic device having a cover device according to an exemplary embodiment.

Referring to FIG. 14, when the rear cover 210 is engaged with the rear case 115 of the body 100, covering the rear case 115, the rear cover 210 may be paired with and connected to the rear case 115. The controller 170 recognizes that the rear cover 210 with the odor detection module 300 has covered the rear surface of the body 100 and controls an activation of a user setting for the odor detection module 300.

Once the user activates the user setting for the odor detection module 300, the odor detection module 300 is operated and detects information about an ambient environment of the electronic device having the cover device 200 (S10). That is, the odor detection module 300 may detect scent, humidity, temperature, and an amount of fine dust in the air. The odor detection module 300 provides a detected value to the controller 170. The controller 170 executes a mode according to the detected value provided by the odor detection module 300 (S20). The controller 170 controls the display 120 to display ambient environment information according to the detected information (S30). For example, if the odor detection module 300 detects the scent of an orange, odor detection module 300 may provide a detected value about the orange to the controller 170, and the controller 170 may display information related to the orange, such as information about when oranges are in season, prices of oranges, a regions that grow oranges, and how the orange is fresh, on the display 120.

Since an odor detection module is provided on the front surface of a cover device, the odor detection module can be miniaturized and, even though the cover device having the odor detection module is provided in an electronic device, the overall size of the electronic device can be minimized.

Since the odor detection device is provided in the cover device, the odor detection device can be connected to the electronic device just by connecting the cover device to the electronic device. Therefore, the portability, aesthetics, and durability of the electronic device can be maintained or enhanced.

Further, as the cover device is engaged with the rear surface of the electronic device and the odor detection device is also connected to the electronic device through the rear surface, a connection device is not externally exposed outward and a connection between the odor detection device and the electronic device can be facilitated. Compared to a conventional odor detector that protrudes at a power/data connection port or an ear-jack connection port of an electronic device and thus is vulnerable to breakage due to frequent connection or impact, one or more exemplary embodiments can reduce the risk of breakage caused by impact or frequent connection and ensure stable connection because the odor detection device is connected to the electronic device by the engagement between the cover device and the rear surface of the electronic device.

When the cover device having the odor detection device is connected to the electronic device, the odor detection device can be activated. As the odor detection device is exposed outwardly from the cover device, the odor detection device can detect accurate data corresponding to the ambient environment (odor, scent, humidity, and temperature), thereby increasing data reliability.

Also, as a scent-emitting cartridge is electrically connected to the cover device having the odor detection device, a scent based on contents of the electronic device, for example, the scent of a rose displayed on the display of the electronic device can be provided to a user by emissions from the scent-emitting cartridge.

While the disclosure has been shown and described with reference to certain exemplary embodiments, it will be understood by those skilled in the art that various changes in form and details may be made therein without departing from the spirit and scope of the disclosure as defined by the claims and their equivalents.

What is claimed is:

1. A cover device protecting an electronic device comprising:
   a rear cover engaged with a rear surface of the electronic device;
   a front cover rotatable with respect to the rear cover, configured to cover a front surface of the electronic device, and comprising an opening;
   an odor detection module mounted to the front cover; and
   a multi-porous member mounted in the opening of the front cover and covering the odor detection module to allow the collection of ambient environment information by the odor detection module.

2. The cover device of claim 1, wherein:
   the opening is formed on a front surface of the front cover, and
   the odor detection module is accommodated in the opening.

3. The cover device of claim 2, wherein the multi-porous member is disposed on a front surface of the opening.

4. The cover device of claim 3, wherein the opening comprises:
   a rear recess for detachably accommodating the odor detection module; and
   a front recess, having a larger area than the rear recess, for accommodating the multi-porous member.

5. The cover device of claim 2, wherein the opening comprises a plurality of porous holes.

6. The cover device of claim 2, wherein
   the front cover comprises:
      a first member having the opening; and
      a second member on a surface of the first member, and
   the odor detection module is mounted between the first member and the second member on a rear surface of the opening.

7. The cover device of claim 1, further comprising a connection module provided in the rear cover configured to connect with a connection terminal in a body of an electronic device to pair the odor detection module with the electronic device.

8. The cover device of claim 7, wherein the connection module comprises:

a connection surface provided on the front cover, and configured to be electrically connected to the odor detection module when the odor detection module is mounted;

a connection member provided on the rear cover and configured to be electrically connected to the odor detection module and the connection terminal of the body; and a connection line provided between the connection surface and the connection member.

9. The cover device of claim 8, wherein the connection member is configured to be electrically connected to at least one of a connection terminal connected at a micro Secure Digital (SD) connection port of a rear surface of the body, a connection terminal connected at a Universal Serial Bus (USB) connection port, a connection terminal connected at an ear jack connection port, and a connection terminal provided separately from connection ports on the rear surface of the body.

10. The cover device of claim 7, wherein the connection module is configured to wirelessly connect with the electronic device using at least one of a Near Field Communication (NFC) connection, a Bluetooth connection, and a ZigBee connection.

11. The cover device of claim 1, further comprising a power supply disposed on the front cover, configured to supply power to the odor detection module.

12. The cover device of claim 11, wherein
a recess is formed around the odor detection module inside the front cover, and
the power supply is configured to be detachably accommodated in the recess formed around the odor detection module.

13. The cover device of claim 1, further comprising a scent-emitting cartridge disposed on the front cover, scent-emitting cartridge configured to emit scent,
wherein, when the rear cover is engaged with a rear surface of a body of an electronic device, the scent-emitting cartridge is paired with the electronic device.

14. A cover device protecting an electronic device comprising:
a rear cover engaged with a rear surface of the electronic device;
a front cover rotatable with respect to the rear cover, configured to cover a front surface of the electronic device, and comprising an opening;
an odor detection module mounted in the opening;
a multi-porous member mounted in the opening and covering the odor detection module to allow the collection of ambient environment information by the odor detection module; and
a connection module configured to, when the rear cover is engaged with a rear surface of a body of the electronic device, pair the odor detection module with an electronic device.

15. The cover device of claim 14, wherein the connection module comprises:
a connection member disposed on the rear cover, electrically connected to the odor detection module, and configured to be electrically connected to a connection port of the body when the rear cover is engaged with the rear surface of the body of the electronic device; and
a connection line provided between the connection member and the odor detection module, and configured to electrically connect the odor detection module to the connection member.

16. The cover device of claim 14, wherein the connection module comprises at least one of a Near Field Communication (NFC) chip, Bluetooth chip, and ZigBee chip.

17. The cover device of claim 14, further comprising a battery on the front cover configured to supply power to the odor detection module.

18. An electronic device having a cover device, the electronic device comprising:
a body;
a rear cover engaged with a rear surface of the body;
a front cover rotatable with respect to the rear cover, configured to cover a front surface of the body, and comprising an opening;
an odor detection module mounted to the front cover;
a multi-porous member mounted in the opening and covering the odor detection module to allow the collection of ambient environment information by the odor detection module;
a connection module configured to pair, when the rear cover is engaged with the rear surface of the body, the odor detection module with the body; and
a controller configured to control the body according to a sensed value of the odor detection module.

19. The electronic device of claim 18, wherein
the body comprises a rear case comprising a battery mounting space on the rear surface of the body, and
the rear cover comprises a cover device configured to cover the rear case.

20. The electronic device of claim 18, wherein
the opening is configured to accommodate the odor detection module, and
the odor detection module is mounted in the opening.

21. The electronic device of claim 20, further comprising a plurality of porous holes provided in the opening.

22. The electronic device of claim 18, wherein the connection module comprises:
a connection member disposed on the rear cover, and configured to electrically connect to the odor detection module and a connection port of the body; and
a connection line provided between the connection member and the odor detection module, and configured to electrically connect the odor detection module to the connection member.

23. The electronic device of claim 22, wherein, when the rear cover is engaged with the rear surface of the body,
the connection member is electrically connected to the connection port, and
the controller is configured to receive a signal corresponding to the electrical connection between the connection member and the connection port and to control an activation of a user module corresponding to the odor detection module.

24. The electronic device of claim 23, further comprising a display,
wherein the odor detection module is further configured to, in response to external information being supplied to the odor detection module through the opening, sense the information, and
wherein the controller is further configured to receive a value corresponding to the sensed information and control the display to display the received value.

25. The electronic device of claim 18, wherein the connection module is further configured to wirelessly pair the body with the odor detection module and operates using at least one of Near Field Communication (NFC), Bluetooth, and ZigBee.

26. The electronic device of claim 25, wherein
the connection module is further configured to, when the rear cover is engaged with the rear surface of the body, pair the body with the odor detection module, and
the controller is further configured to receive a pairing signal from the connection module and control an activation of a user module corresponding to the odor detection module.

27. The electronic device of claim 18, further comprising a battery disposed on the front cover and configured to supply power to the odor detection module.

28. The electronic device of claim 18, further comprising:
a display; and
a scent-emitting cartridge provided in on the front cover, and configured to emit scents,
wherein, when the rear cover is engaged with the rear surface of the body,
the scent-emitting cartridge is connected to the body, and
the controller is further configured to control the scent-emitting cartridge according to information displayed on the display.

\* \* \* \* \*